US012599426B2

(12) United States Patent     (10) Patent No.:   US 12,599,426 B2
Janich et al.     (45) Date of Patent:     Apr. 14, 2026

(54) ELECTROSURGICAL GENERATOR HAVING AN EXTENDED MEASUREMENT RANGE

(71) Applicant: OLYMPUS WINTER & IBE GMBH, Hamburg (DE)

(72) Inventors: Fabian Janich, Potsdam (DE); Jens Krüger, Zeuthen (DE); Daniel Ramin, Nuthetal (DE); Frank Breitsprecher, Berlin (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 498 days.

(21) Appl. No.: 18/077,051

(22) Filed: Dec. 7, 2022

(65) Prior Publication Data

US 2023/0210578 A1     Jul. 6, 2023

Related U.S. Application Data

(60) Provisional application No. 63/286,902, filed on Dec. 7, 2021.

(51) Int. Cl.
    *A61B 18/12*        (2006.01)
    *A61B 18/14*        (2006.01)
    *A61B 18/00*        (2006.01)

(52) U.S. Cl.
    CPC .......... *A61B 18/1206* (2013.01); *A61B 18/14* (2013.01); *A61B 2018/00702* (2013.01); *A61B 2018/00892* (2013.01)

(58) Field of Classification Search
    CPC ................ A61B 18/1206; A61B 18/14; A61B 2018/00642; A61B 2018/00702;
             (Continued)

(56) References Cited

U.S. PATENT DOCUMENTS 6,165,169 A * 12/2000 Panescu ............. A61B 18/1492
                                              606/1
8,610,501 B2 * 12/2013 Gilbert ............... A61B 18/1206
                                              330/251

(Continued)

FOREIGN PATENT DOCUMENTS

EP        2 322 108 B1     8/2015

OTHER PUBLICATIONS

Aug. 12, 2022 Office Action issued in German Patent Application No. 10 2021 132 365.7.

*Primary Examiner* — Michael F Peffley
(74) *Attorney, Agent, or Firm* — OLIFF PLC.

(57) ABSTRACT

An electrosurgical generator for supplying power, including an inverter for high voltage, which is led to an output to the connector of an electrosurgical instrument, a measurement system with at least one measurement monitor for a physical parameter at the output or at the electrosurgical instrument, and an operation controller which controls the inverter on the basis of at least one predefined operating sequence. The measurement monitor for the physical parameter is switchable between a plurality of different configurations which differ in the measurement range. The operation controller interacts with the measurement system so one of the different configurations of the measurement monitor is switched in each case, under control by the operating sequence. By switching the configuration, the suitable measurement range is always set during operation. Apparently contrariwise requirements in relation to a reliable measurement even at high amplitudes are linked with great measurement accuracy even at low amplitudes.

17 Claims, 2 Drawing Sheets

(58) Field of Classification Search
   CPC ........... A61B 2018/00779; A61B 2018/00791;
                A61B 2018/00827; A61B 2018/00869;
                A61B 2018/00892; A61B 2018/126
   See application file for complete search history.

(56) References Cited

U.S. PATENT DOCUMENTS

| | | | |
|---|---|---|---|
| 2006/0020261 A1* | 1/2006 | Refior | A61B 18/1206 |
| | | | 606/34 |
| 2011/0071521 A1* | 3/2011 | Gilbert | H03H 17/0664 |
| | | | 606/42 |
| 2016/0011244 A1* | 1/2016 | Buck | A61B 18/1206 |
| | | | 324/76.11 |

\* cited by examiner

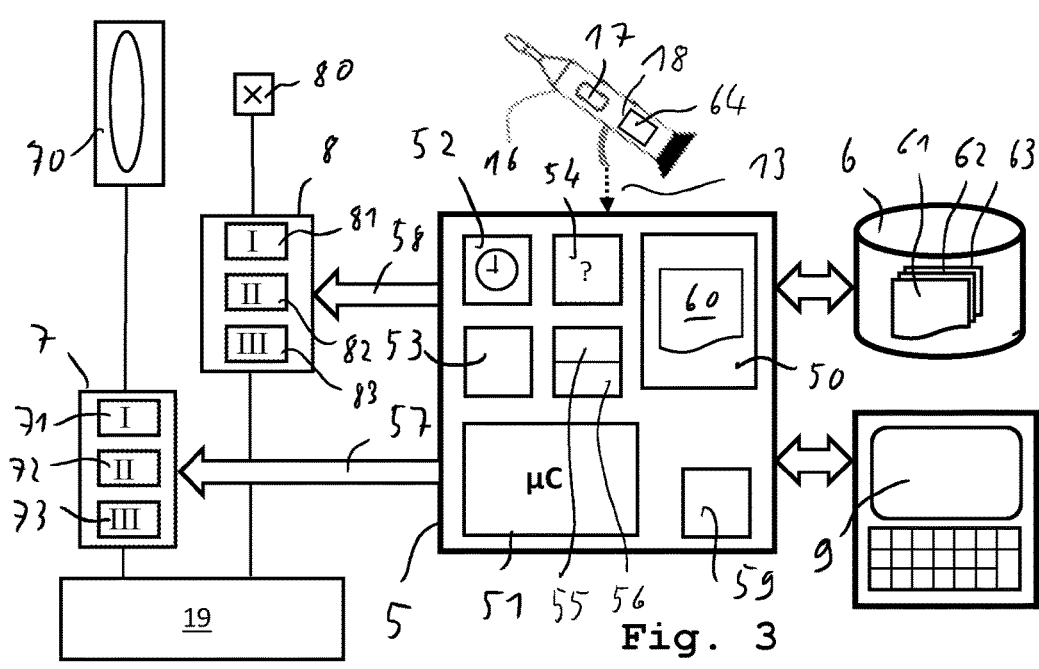
Fig. 3
| U Monitor | I Monitor | Range | | | | Ok |
|---|---|---|---|---|---|---|
| | | U [V] | U_peak [V] | I [mA] | I_peak [mA] | |
| I | I | 0 − 580 | 0 − 4440 | 0 − 3800 | 0 − 28000 | + |
| I | II | 0 − 580 | 0 − 4440 | 0 − 1400 | 0 − 10500 | + |
| I | III | 0 − 580 | 0 − 4440 | 0 − 560 | 0 − 4100 | + |
| II | I | 0 − 450 | 0 − 1500 | 0 − 13500 | 0 − 28000 | + |
| II | II | 0 − 450 | 0 − 1500 | 0 − 4750 | 0 − 10500 | + |
| II | III | 0 − 450 | 0 − 1500 | 0 − 1900 | 0 − 4100 | + |
| III | I | 0 − 150 | 0 − 370 | 0 − 13500 | 0 − 28000 | + |
| III | II | 0 − 150 | 0 − 370 | 0 − 4750 | 0 − 10500 | + |
| III | III | 0 − 150 | 0 − 370 | 0 − 1900 | 0 − 4100 | + |
Fig. 4
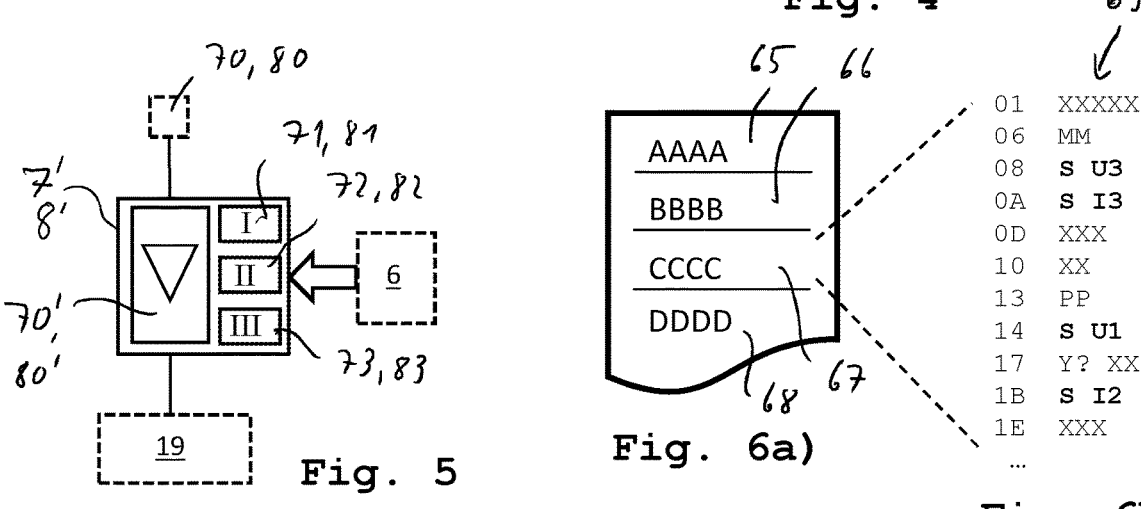
Fig. 5
Fig. 6a)
Fig. 6b)

ELECTROSURGICAL GENERATOR HAVING AN EXTENDED MEASUREMENT RANGE

The invention relates to an electrosurgical generator designed to output a radiofrequency AC voltage to an electrosurgical instrument. It comprises a measurement system which comprises at least one measurement monitor for output voltage and/or current, and an operation controller which controls the inverter on the basis of at least one predefined operating sequence.

In electrosurgery or radiofrequency surgery, radiofrequency alternating current is introduced into a tissue of the human body by means of an electrosurgical instrument, such as an electrical scalpel. In particular, the tissue is cut or severed by means of the heat caused thereby. An advantage here is that the incision can be simultaneously also accompanied by hemostasis as a result of sealing of the affected vessels, and electrosurgical instruments come into question for further types of application, such as for coagulation.

By all means, this requires considerable powers, to be precise at frequencies of 200 kHz or more, up to 4000 kHz and typically around 400 kHz. Body tissue acts like an ohmic resistor at such frequencies. However, the resistivity depends significantly on the type of tissue; for example, the resistivities of muscles, fat and bone deviate significantly from one another, to be precise by up to a factor of 1000. As a result, the load impedance of the electrical scalpel may vary significantly and quickly during operation depending on the tissue to be cut, starting from virtually infinity when the instrument is brought close to the tissue down to a virtual short circuit. This places particular and unique requirements on the electrosurgical generator and, in particular, its high-voltage provision and the control thereof, which do not occur like this in other fields of technology.

To meet these unique requirements, electrosurgical generators are constructed so that they comprise an inverter for supplying power to the electrosurgical instrument, the instrument being supplied with rectified current. Typically, the inverter is embodied as a free-running single-ended generator with an LC resonant circuit. This structure has proven its worth. Further, the applicant has developed a type of electrosurgical generators which provide a multilevel inverter as inverter. This allows frequency, amplitude and waveform of the generated AC voltage to be set largely freely, with the high voltages required being achieved by an output transformer.

In view of the sensitivity of the tissue treated by the electrosurgical generator with the instrument connected thereto, precise monitoring and control of the output radiofrequency energy is required. An accurate measurement system is required to this end. The latter needs to be matched to the electrosurgical generator and its performance. Newly developed electrosurgical generators have increased performance. The voltage and current ranges to be covered by the measurement system are becoming larger. However, measurement systems for large voltage ranges have the disadvantage of measuring rather inaccurately at low voltages.

Further, modern electrosurgical generators ever more frequently have specialized operating sequences (what are known as modes) for different applications. For example, the application of a coagulation that reaches into the depth of the tissue requires low voltages in terms of value (of the order of approximately 200 V peak voltage), while significantly higher voltages (of the order of 1200 V peak voltage) are used for a pure cutting mode for the severing of tissue. By contrast, if a rather large-area coagulation should be used, for example to stop diffuse surface bleeding, use is made of a special coagulation mode (e.g., spray mode) which makes use of very high voltages (of the order of 4000 V peak voltage), albeit in a modulated waveform with a low duty cycle (approximately 1:10).

Consequently, the requirements in respect of the measurement system are becoming ever more extensive. To be able to cover high regions of the high voltage as well, there is the risk of increasing inaccuracy in lower regions of the high voltage. Although it would be possible to provide a plurality of measurement systems in one electrosurgical generator, this would lead to an unjustifiable increase in the production outlay.

The invention is based on the object of developing an electrosurgical generator with an improved measurement system and a corresponding operating method, which allows a greater measurement range to be covered without loss of accuracy.

The solution according to the invention is found in the features of the independent claims. Advantageous developments are the subject matter of the dependent claims.

In an electrosurgical generator for supplying power to an electrosurgical instrument by way of radiofrequency AC voltage, comprising an inverter for high voltage, which is led via an output line to an output to the connector of the electrosurgical instrument, a measurement system which comprises at least one measurement monitor for a physical parameter at the output or at the electrosurgical instrument, and an operation controller which controls the inverter on the basis of at least one predefined operating sequence, provision is made according to the invention for the measurement monitor for the physical parameter, in particular voltage, current, frequency, phase, force, temperature, and/or power, to be switchable between a plurality of different configurations which differ in terms of their measurement range, the operation controller interacting with the measurement system such that one of the different configurations of the measurement monitor is switched in each case, under control by the operating sequence.

Advantageously, provision is made for the measurement monitor to be embodied as a measurement monitor for the output voltage and be switchable between a plurality of different configurations which differ in terms of their voltage measurement range, and/or for the measurement monitor to be embodied as a measurement monitor for the output current and be switchable between a plurality of different configurations which differ in terms of their current measurement range.

First, some of the terms used are to be explained:

A measurement monitor is understood to mean a signal processing unit, in particular a measurement amplifier, which is connected to the actual sensor, in particular measurement transducer, and which is used for the measurement signal of the sensor.

In particular, the physical parameter detected by the measurement monitor is a parameter which is found at the output or at the instrument connected there and which influences the effect of the electrosurgical generator or its instrument on the tissue to be treated. In particular, this is an electrical parameter such as the output voltage and/or the output current. The voltage can be the effective value, the peak voltage and/or the DC voltage component; for the current, the effective value, peak current and/or direct current component applies accordingly. Measurement monitors may be provided to this end. Further, a measurement monitor may be provided for frequency and/or phase (phase difference) or other AC voltage-related variables (e.g., waveform, total harmonic distortion, etc.). A measurement monitor for frequency may be very important, especially for electrosurgical generators with a free-running inverter. Moreover, in addition or as an alternative, provision can be made for one or more measurement monitors for the output power, such as for the apparent power, active power, and/or reactive power. Further, it may be advantageous to provide one or more measurement monitors for physical parameters specifically on the instrument, in particular for the force, for example the clamping force between jaws of a bipolar electrode of the instrument or a contact-pressure force of the electrode on the tissue, and/or for the temperature at the electrode of the instrument and/or the treated tissue (e.g., by means of an IR radiation-based thermal sensor).

"Different configurations" are understood to mean signal processing units of the measurement monitor which are configured differently from one another and to which the measurement signal can alternatively be applied. The signal processing units are differently configured when, in particular, they differ in terms of their signal processing structure and/or their parameterization.

In relation to the measurement monitor, "switching" is understood to mean that the measurement signal from the sensor is applied to the respective configuration. A "switchover" is understood to mean that the measurement signal interacts with one of the other, differently configured signal processing units. This may consist in a different one of a plurality of different signal processing units being connected, and/or in the connected signal processing unit being configured differently, in particular a parameter of the signal processing unit essential to the measurement operation being altered. In the case of a measurement amplifier, the gain factor thereof in particular is an example for the change of such an essential parameter.

"High voltage" is typically understood to mean voltages up to 10 kV, preferably up to 5000 V.

In the field of electrosurgical generators, "radiofrequency" frequencies are typically understood to be frequencies ranging from 200 kHz to 4000 kHz.

The power provided by the electrosurgical generator is typically in the range between 1 and 500 watts, with the load impedance being able to vary significantly and, accordingly, the output voltage and power output likewise being able to vary significantly and quickly. In order to be able to detect this quickly and accurately, high demands are placed on the measurement systems and its measurement monitors.

The concept of the invention lies in the idea of obtaining an adaptation of the measurement system to the measurement ranges for voltage/current to be covered in each case by way of switching over the configuration of the measurement monitor. Consequently, the suitable measurement range can always be set depending on the specific requirements during the operation of the electrosurgical generator. This enables a highly accurate measurement over the entire range from small to large amplitude of the physical parameter to be measured by way of switching over to the respective suitable configuration of the measurement monitor (e.g., having in each case a configuration for low voltage, a configuration for mid voltage and a configuration for high voltage in the case of a measurement monitor for voltage, and a corresponding situation in the case of a measurement monitor for current). This is explained in exemplary fashion using the example of measurement monitors for voltage and current (a corresponding situation applies for other physical parameters to be measured). By switching over the configuration, it is possible to carry out an accurate measurement, starting from small values for voltage or current up to large values for high voltage or high current. Consequently, the apparently contrariwise requirements in relation to a reliable measurement even at high amplitudes of the high voltage or of the current are linked with great measurement accuracy even at low voltage or current amplitudes. Thus, with little outlay, the invention achieves a considerable increase of the measurement range without this being to the detriment of the accuracy. Consequently, a very accurate voltage or current measurement can always be obtained even in the case of very different operating sequences with completely different requirements in relation to the voltage level or current level to be measured, this being a precondition for a correct power output of the electrosurgical generator in the interest of protecting the patient. Corresponding statements apply in relation to other measurement monitors according to the invention for other physical parameters, in particular frequency, phase, force, temperature, and/or power, at the output or at the electrosurgical instrument.

Further, the protection of the patient can be improved by virtue of this switchover being implemented on the basis of the chosen operating sequence. This ensures that it is always the measurement range that fits the chosen operating sequence that is set. This effectively counteracts the risk of operator errors, further increasing the safety for the patient.

Advantageously, provision is made for the at least one operating sequence to be selectable by a user from a set of predetermined operating sequences. A further field of application for the electrosurgical generator can be obtained by the provision of a set of envisaged operating sequences. Especially if this field of application covers both applications with significant high voltage and those with low voltage or applications with high currents and those with low currents, the advantages of the switchover according to the invention of the configuration of the measurement monitors on the basis of the operating sequence take full effect.

Advantageously, provision is made for the at least one operating sequence and/or the predefined operating sequences to each comprise control data for an automated selection and switching between the various configurations of the measurement monitors. By providing appropriate control data in the operating sequences, it is possible to adapt the selection from the various configurations to the requirements of the respective operating sequence in each case. This applies both in relation to the initial selection and in relation to subsequent switching over during the execution of the operating sequence. This allows a fine adjustment to be carried out in relation to the voltage and current conditions of the various operating sequences, with even multiple switchovers optionally being able to be carried out automatically during the operating sequence in the case of more complex operating sequences.

In this case, it is particularly advantageous if the various configurations of the measurement monitors are preferably switched in a predetermined sequence, according to which the various configurations of the measurement monitor or monitors (e.g., for voltage and/or current) are selected in succession, with sequence and/or times of the switchover between the various configurations being determined by the at least one operating sequence and/or the predefined operating sequences.

Thus, even operating sequences which start for example with low voltage and/or current in an initial phase can be correspondingly switched to more sensitive configurations of the measurement monitors for relatively small measurement ranges, whereas there is accordingly then a switchover to configurations for larger voltage and/or current ranges in a subsequent phase of the operating sequence in which higher voltage and/or currents are used. What this type of switchover can achieve is that configurations of the measurement monitors that are optimally adapted are selected and active for the measurement system at all times and in every situation. Thus, even during an operating sequence with successive, substantially varying voltage and/or current ranges, the respective measurements are always carried out with the highest possible accuracy. The radiofrequency power output by the electrosurgical generator can thus be determined with the greatest precision, which causes a correspondingly higher quality of the surgical activity carried out with the instrument.

To this end, the operating sequences preferably comprise time control data which each specify times for connecting up and/or switching between the different configurations of the measurement monitor or monitors. Consequently, it is possible to obtain precise time control in relation to the switchover of the configurations within the scope of the operating sequence. As an alternative or in addition, provision is advantageously made for the operating sequences to comprise event control data which each specify event conditions for connecting up and/or switching between the different configurations. Consequently, it is possible to react to events, such as the attainment of a certain voltage or the detection of a certain state, for example the presence of plasma ignition at the instrument etc., in the sequence of switching over the configurations. In this way, the adaptation to the operating sequences can be optimized, and it is always possible to switch to the optimally fitting configurations of the measurement monitor or monitors in each case even for complex operating sequences.

Optionally, provision can be made here for signal feedback to be provided for at least one event condition. This makes it possible to react to actual conditions as currently present at the electrosurgical generator or at the instrument. In particular, this can be a signal for the temperature present at the instrument, for the force exerted by the instrument on tissue to be treated or for a clamping force between jaws of a bipolar electrode of the instrument, for identifying carbon at the instrument and/or for identifying an ignition state of plasma at the instrument. By way of example, a significant increase in the output electric power may be detected within the scope of an operating sequence that provides for the formation and ignition of a plasma at the instrument and be used as event condition for an onset of plasma ignition; subsequently, the configurations of the measurement monitors can then be suitably switched over. Thus, optionally provision can also be made for the signal feedback to comprise an ignition state of the instrument. This allows direct reaction to the event of the onset of plasma ignition and implementation of a switchover of the configurations of the measurement monitors in accordance with the operating sequence. This brings about a particularly fast switchover of the configurations of the measurement monitors which has been adapted to the situation. It is understood that other types of event conditions may also be provided.

The switchover of configurations of the various measurement monitors (for example for voltage and current) can be implemented together. However, this is not mandatory and provision can preferably be made for the switchover of configurations of one of the measurement monitors, preferably of the measurement monitor for voltage, to be implemented independently of the switchover of configurations of another one of the measurement monitors, preferably of the measurement monitor for current. Consequently, the respective configurations of the various measurement monitors can be switched over independently of one another at different times (or in the case of different events). This facilitates a more precise adaptation to transitions, especially in the case of a complex operating sequence.

At this point, reference is made to the fact that the initial connecting up of the configurations of the measurement monitors is part of the invention, but a subsequent switchover from one configuration of the measurement monitors to another during the operating sequence is not mandatory. Optionally, the invention may also provide for the switched configuration of the measurement monitors selected by an operating sequence to be maintained for the duration of this operating sequence, that is to say there is no switchover. If there is a transition to another operating sequence, there can naturally be a switchover again.

Further, a switching state matrix can advantageously be provided, in which admissible configurations of the measurement monitor or monitors, in particular admissible combinations of configurations of a plurality of the measurement monitors, such as configurations of the measurement monitor for voltage with configurations of the measurement monitors for current, are defined, and, preferably, inadmissible configurations or combinations of the configurations are temporarily or permanently blocked. This makes it possible to block certain configurations or combinations of configurations of the measurement monitors. This may be advantageous if only configurations determined in advance are admissible at least for some types of electrosurgical generators, for example only configurations I, II for the voltage measurement monitor for a first type of generator and by contrast only configurations II, III for the voltage measurement monitor for a second type of generator. Further, this can also preclude certain combinations of configurations, for example those configurations that should be avoided because there would otherwise be the risk of overloading the measurement monitors. This may be advantageous, in particular, in the case of relatively small electrosurgical generators within a series: the combination is blocked for these while larger electrosurgical generators with more robust measurement monitors allow this combination. The risk of damage to the (relatively small) electrosurgical generator by switching such a disadvantageous combination of the measurement monitors can thus be avoided. The preclusion or blocking of configurations or combinations of configurations may be provided permanently or optionally only temporarily, for example by virtue of a blocking time being saved in the switching state matrix. The latter is advantageous, in particular, for avoiding overheating in the case of a high load.

Further, a state detector for the measurement monitors may be provided which is designed to recognize a defect of the measurement monitors, and, further, provision can be made for a replacement switching unit which interacts therewith and which by way of a replacement switches a different configuration with a larger measurement range, which uses other components or a different signal processing unit, should a defect of a configuration of the measurement monitor be recognized (for example, as a result of an outage of the corresponding signal processing unit). Consequently, the corresponding measurement is not lost even in the case of such a defect, but instead it can then be adopted by another one of the configurations, preferably the configuration with the next largest measurement range. Although a certain deterioration in the measurement accuracy accompanies this as a consequence of the measurement range now too large per se, in return the electrosurgical generator can still be used in the affected operating sequence despite the defect.

Preferably, the electrosurgical generator further comprises a processor and a computer-readable data medium on which instructions are stored, the instructions causing the at least one operating sequence to be carried out when executed by the processor. Stored on the data medium are the instructions which, upon execution by the processor, bring about the selection and switching of or switching between the respectively provided configurations of the measurement monitors. Consequently, there can be an efficient, simple to handle expansion of the operating sequences depending on the computer-readable storage medium. In particular, provision can be made for additional operating sequences to be able to be carried out by the electrosurgical generator, for example by virtue of these being saved on the electrosurgical instrument. To this end, the electrosurgical generator reads, during operation, the operating sequence stored on the electrosurgical instrument and carries the latter out, with the respective configurations of the measurement monitors then being selected and switched so as to fit precisely to this electrosurgical instrument. This not only enables a subsequent expansion with further, additional operating sequences, but also ensures an optimal adaptation to the respectively used electrosurgical instrument. To this end, the user need not carry out any more than connect the electrosurgical instrument to the electrosurgical generator, and the operating sequence is automatically saved and called. This minimizes the risk of operator errors.

Advantageously, the at least one operating sequence is configured as a data set with structured data. The structured data comprise a multiplicity of parameterized pointers that point to control commands stored in the electrosurgical generator. Values for parameters that specify control interventions may also be contained in the structured data. During the operating sequence, the parameterized pointers stored in the structured data are called by means of the processor and the saved control commands, to which the parameterized pointers represented by the structured data point, are executed. Should the structured data contain values for operating parameters, the control commands are executed taking account of these operating parameter values specified in the structured data. Advantageously, the structured data contain switching control data for connecting up, in particular also for switching between, the various configurations of the measurement monitors of the electrosurgical generator. This can bring about a flexible and adapted and optionally easily changeable mode of operation of the electrosurgical generator.

The invention further relates to a system comprising the electrosurgical generator as described above and an electrosurgical instrument, wherein, preferably, the predefined operating sequence is selectable from a set of operating sequences, which are saved in the electrosurgical generator or the electrosurgical instrument. Consequently, the electrosurgical instrument can bring about an expansion in relation to the operating sequences. In particular, this offers the advantage of an electrosurgical instrument having saved thereon the operating sequence suitable therefor, the latter being read by the electrosurgical generator when the instrument is connected up thereto and being executed by the processor. Further, this offers significant future-proofness since this allows a new electrosurgical instrument to also introduce further operating sequences, which fit to this instrument, onto an already available (older) electrosurgical generator. This yields significant advantages in respect of operational safety and future-proofness.

Preferably, provision is further made for the electrosurgical instrument to have a machine-readable instrument identity indicator which characterizes the instrument, and for the system to comprise a control device which enables one or more operating sequences from the set of operating sequences depending on the instrument identity indicator. This can reliably ensure that only operating sequences fitting to the specific connected instrument are executed and hence the configurations of the measurement monitors are also switched accordingly. The risk of faults on account of a wrong unsuitable instrument, which might lead to damage to the equipment and/or to a risk to the patient, is thus effectively prevented.

Further, the invention extends to a corresponding method for operating the electrosurgical generator comprising an inverter for high voltage, which is led via an output line to an output to the connector of the electrosurgical instrument, a measurement system which comprises at least one measurement monitor for a physical parameter, in particular voltage, current, frequency, phase, force, temperature, and/or power, at the output or at the electrosurgical instrument, with the inverter being controlled by an operation controller on the basis of at least one predefined operating sequence, wherein, according to the invention, provision is made for switching during operation between a plurality of different switchable configurations of the measurement monitor which differ in terms of their measurement range, with the switching of a respective one of the different configurations of the measurement monitor for the physical parameter being controlled by the operating sequence.

Hence, the respective fitting configuration of the measurement monitor for the physical parameter is used as a result of the switching by the operating sequence. So as to avoid repetitions, the description above is referred to in relation to a more detailed explanation.

The invention will be explained in more detail below on the basis of an advantageous exemplary embodiment, with reference being made to the attached drawing, in which:

FIG. 3 shows a functional diagram in relation to a measurement system with switchable configurations of the measurement monitors and a processor;

FIG. 4 shows a table with measurement ranges and combinations for various configurations of the measurement monitors;

FIG. 5 shows an alternative embodiment relating to the switchable measurement monitor; and FIGS. 6a, b show a schematic representation of structured data for an operating sequence with a detailed representation.

Figure 1:
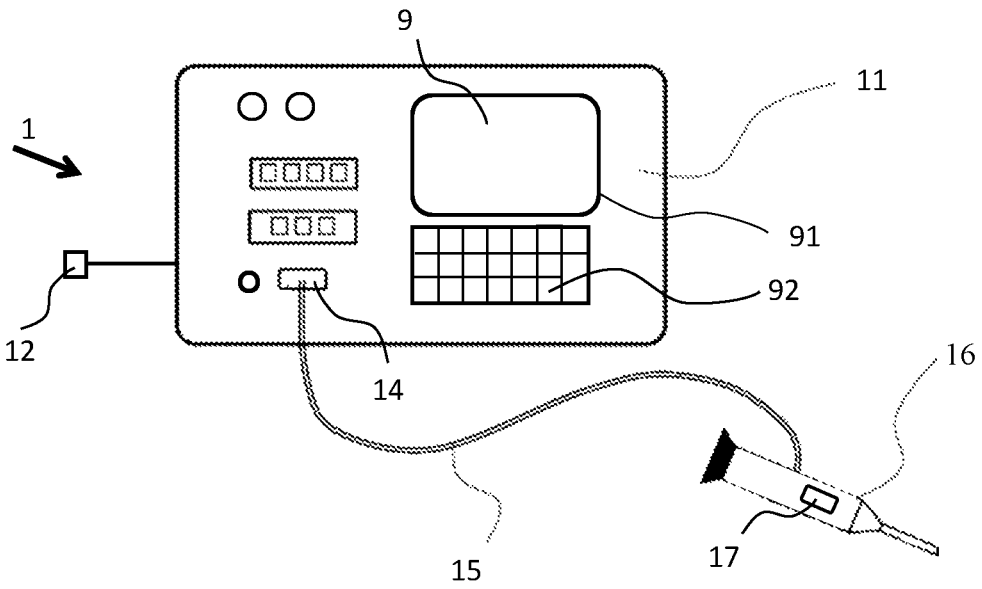
FIG. 1 shows a schematic representation of an electrosurgical generator according to an exemplary embodiment with a connected electrosurgical instrument.

An electrosurgical generator according to an exemplary embodiment of the invention is depicted in FIG. 1. The electrosurgical generator denoted by reference sign 1 in its totality comprises a housing 11 which is provided with an output port 14 for an electrosurgical instrument 16. In the exemplary embodiment depicted, the electrosurgical instrument 16 is an electrical scalpel. It is connected via a high-voltage-proof connecting cable 15 to the output port 14. Operation of the electrosurgical generator 1, and hence also setting of the power for the electrosurgical instrument 16, is implemented by way of an operating device 9. The latter comprises a display screen 91 and an input unit 92. This allows the functions of the electrosurgical generator 1 to be set. The operating device 9 is connected to an operation controller 10 of the electrosurgical generator 1. It controls the individual components and units of the electrosurgical generator 1 and monitors the operation. Thus, it is possible, in particular, to call an operating sequence stored in the electrosurgical generator 1 or the instrument 16 by means of the operating devices 9, the operating sequence then being executed accordingly by the operation controller 10. The latter comprises a processor 5, which will be explained in more detail below.

Figure 2:
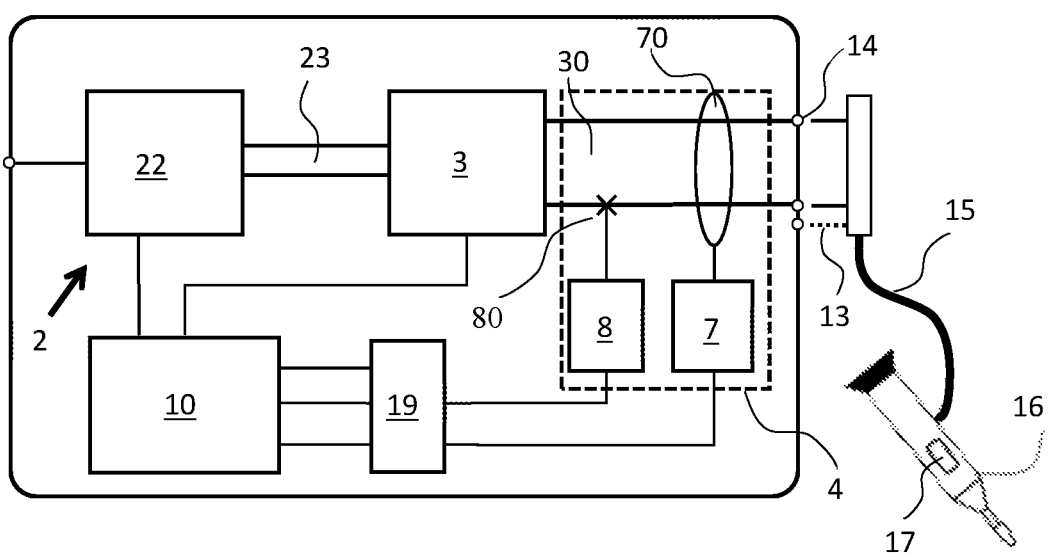
FIG. 2 shows a block diagram relating to the electrosurgical generator according to FIG. 1.

For the subsequent explanation of the structure of the electrosurgical generator 1, reference is made to FIG. 2 in particular. A DC voltage supply 2 is provided for supplying the electrosurgical generator 1 with power. The latter may be connected to the public power grid via a grid connector cable 12 and may comprise a high voltage power supply (HVPS) 22. The power supply 22 comprises a rectifier and supplies a DC link 23 with power in the depicted exemplary embodiment. Attention is drawn to the fact that the supply of power from a power supply 22 is not mandatory, but that other types of DC voltage supply 2 also come into consideration, for example a direct supply with direct current, especially in the case of electrosurgical generators installed in vehicles or in the case of such electrosurgical generators as are provided in mobile or temporary hospitals.

The level of the DC voltage is typically between 10 and approximately 500 volts, frequently 48 volts in the case of modern electrosurgical generators. It may be fixed or variable, this depending in particular on the type of inverter 3 that generates the high voltage. The absolute level of the DC voltage may depend, in particular, on the set power, the type of electrosurgical instrument 16 and/or the load impedance thereof, the latter in turn depending on the type of tissue treated.

An inverter 3 is supplied with power by the DC voltage supply 2 and produces radiofrequency AC voltage in the high-voltage range of a few kilovolt, with frequencies ranging between 200 kHz and 4 MHz, from the supplied DC voltage. By way of example, what is known as a single-ended converter which is controlled in free-running fashion by an oscillator may be provided as an inverter 3; as a rule, it is supplied with variable voltage by the DC voltage supply 2. This embodiment can post the advantage of conceptual simplicity and, as a rule, directly leads the generated high voltage via an equipment-internal output line 30 to the output port 14 for the electrosurgical instrument 16. —Alternatively, however, provision can also be made for the inverter 3 to be configured as a power inverter. In the latter, the power and the voltage to be output are set by way of the power inverter itself, and so there is no need for a variable DC voltage supply 2; instead, a supply with fixed voltage (e.g., 48 volts) is sufficient. The power inverter has power semiconductor switches as what are known as current valves, which are controlled by a power inverter controller (not depicted here) in a manner known per se, for example by means of pulse width modulation, which is known as PWM control, for the purposes of generating a radiofrequency high voltage. The radiofrequency high voltage generated by the power inverter is consequently virtually freely adjustable in respect of frequency and waveform. The radiofrequency voltage generated by the power inverter is typically output via a low pass filter and an output transformer (not depicted) for voltage increase to the generator-internal output line 30 to the port 14 for the electrosurgical instrument 16.

To measure the power output to the instrument 16 by the electrosurgical generator 1, the voltage and power of the high voltage generated by the inverter 3 are measured by means of a measurement system 4. Measurement transducers 70 and 80 are connected to the output line 30 and, as sensors, detect the voltage output, or the current flowing, to the electrosurgical instrument 16 at the output port 14. The measurement transducer for voltage 70 is connected to a measurement monitor 7 for voltage. The latter acts as a measurement circuit and is designed for the signal processing of the measurement signal from the measurement transducer 70. The thus determined signal for the measured voltage is output at an output of the measurement monitor 7 and is applied to an input of a monitoring unit 19, which in turn is connected to the operation controller 10 of the electrosurgical generator 1. Accordingly, the measurement transducer for current 80 is connected to a measurement monitor 8 for current, which acts as a measurement circuit and is designed for the signal processing of the measurement signal from the measurement transducer 80. The thus determined signal for the measured current is output at an output of the measurement monitor 8 and is applied to a further input of the monitoring unit 19. From the applied signals for the measured voltage and the measured current, the monitoring unit 19 determines the power output via the output port 14 to the instrument 16 and transmits these three parameters (power, voltage and current) to the operation controller 10. The latter can consequently monitor the output power, voltage and current. In particular, the operation controller 10 can act on the inverter 3 in order to readjust in relation to the output voltage and/or current such that the values required by the operating sequence are obtained.

The high voltage generated by the inverter 3 and the high voltage led via the output line 30 to the port 14 is output to the instrument 16, which is interchangeably connected to the port 14 via the high-voltage-proof connecting cable 15. Optionally, the instrument 16 may further be connected to the electrosurgical generator 1 at the port 14 via a data line 13. Additional data can be transmitted from the instrument 16 to the electrosurgical generator 1 via this data line, in particular information about an instrument ID 17 stored in a memory of the instrument 16 and/or a special operating sequence 64 that is likewise saved in the instrument 16 and suitable for the respective instrument 16.

Reference is now made to FIG. 3, which shows a functional diagram. A plurality of different operating sequences are saved in a data memory 6 of the electrosurgical generator 1; these are symbolized in the present case by three saved operating sequences 61, 62, 63. Thus, provision can be made for the instrument 16 itself to have saved in a dedicated memory 18 a special operating sequence 64 suitable for this instrument 16. When the instrument 16 is connected to the port 14, this special operating sequence 64 is read by the processor 5 via the data link 13 and can subsequently be activated. It is understood that even a plurality of such operating sequences can be saved in the instrument 16. Further, there is the option of saving additional operating sequences from other external sources in the data memory 6 of the electrosurgical generator 1 via interfaces that are not depicted. By way of the operating device 9, the user may select one of the operating sequences, and the latter is loaded into a data medium 50 for execution processes by way of a processor 5, which is part of the operation controller 10.

In the exemplary embodiment of the invention described here, the measurement monitors 7, 8 for voltage and current are switchable between a plurality of different configurations. To this end, the measurement monitor 7 for voltage has a plurality of differently configured signal processing units 71, 72, 73, which total three in the depicted example. They are also referred to as configurations I, II, III for short. Accordingly, the measurement monitor 8 for current also has differently configured signal processing units 81, 82, 83, which likewise total three in the depicted example. They form different configurations I, II and III in relation to the measurement monitor 8 for current. In the depicted exemplary embodiment, the configurations I, II, III differ from one another by virtue of in each case configuring different measurement ranges of the measurement monitor 7 or 8. The total of nine combination options arising from the two measurement monitors 7, 8 with three configurations each are listed in the rows of the table of FIG. 4. The last column of the table specifies whether this is an admissible and operational combination. This forms a switching state matrix 59, which indicates whether a combination is admissible and operational. All combinations are admissible and operational in the depicted exemplary embodiment, with this being indicated by the displayed plus symbol—should a configuration for a measurement monitor 7, 8 or a certain combination not be admissible or not be operational, then the column would depict a minus symbol and the corresponding configuration or combination would thus be blocked. This has the consequence that the switchover signals for switching between such blocked measurement monitors or combinations are blocked.

The table according to FIG. 4 further depicts the values belonging to configurations I, II, III for the measurement range of the voltage and the measurement range of the current, respectively, and the respective admissible associated peak values ("peak") for voltage and current, respectively. Column 3 specifies the measurement ranges for the measurement monitor 7 for voltage and column 4 specifies the respective admissible peak values of the voltage in the various configurations I, II and III. It is evident that the highest dielectric strength exists in configuration I, where the peak value reaches up to 4400 V. Accordingly, column 5 specifies the measurement ranges for the measurement monitor 8 for current and column 6 specifies the respective admissible peak values for the currents in the various configurations I, II and III of the current measurement monitor 8.

The appropriate configuration I, II or III is set on each measurement monitor 7, 8 by way of control commands of the processor 5. The latter comprises a processing unit 51 which evaluates the control data contained in the selected and active operating sequence 60 and which accordingly sets the configuration of the measurement monitors 7, 8 via signal lines 57, 58.

To this end, the operating sequences 60, 61, 62, 63, 64 comprise structured data in the depicted exemplary embodiment. An example for the basic structure thereof is depicted in FIG. 6*a*. As main components they comprise a data block 65 for defining the application ranges with a description, a data block 66 for defining the hardware requirements, a data block 67 for setting and defining the actual operating sequence ("mode"), and a data block 68 with specifications regarding compatible instruments 16.

The data block 67 for setting and defining the actual operating sequence is of particular interest here. An example with a detailed representation of a data set of structured data is depicted in FIG. 6*b*. This relates to a sequence of steps for the operating sequence numbered in hexadecimal. At the start there is a first segment of the operating sequence which contains at least one general control command (symbolized by a row with "X" signs). Subsequently, a second segment of the operating sequence is introduced in the next line in the depicted example. To this end, the data set contains a control command ("MM") for the start of a measurement phase, wherein the measurement monitor 7 for voltage (U) is switched (S) into the third (3) configuration III ("S U3") and the measurement monitor 8 for current (I) is likewise switched into the third configuration ("S I3"), as specified in the two subsequent rows in FIG. 6*b*. This then is followed by further (two in the depicted example) general control commands (once again symbolized by the "X" signs). Subsequently, a second segment of the operating sequence is introduced. To this end, the data set contains a control command ("PP") for the start of a power phase, wherein, first of all, only the measurement monitor 7 for voltage is switched over into another configuration ("S U1"), specifically into the first configuration I. The measurement monitor 8 for current still remains unchanged. Now, the occurrence of a certain event ("Y") is checked in the next step in the depicted example. If said event occurs, then the measurement monitor 8 for current is switched over into another configuration ("S I2"), specifically into the second configuration II, in the subsequent step. This is followed by further control commands and, optionally, further switchovers (not depicted) of the measurement monitors. Consequently, switchovers of the configurations of the measurement monitors 7, 8 can be automatically carried out in an automated fashion as defined by the operating sequence.

During this operating sequence, the switchover is implemented on the basis of event control data (in event-controlled fashion), as defined by the control data in line 17. To this end, an event detector 53 is provided at the processor 5. The event detector 53 may be designed to monitor the occurrence of certain events in the electrosurgical generator 1 (further, the attainment of a certain voltage or a predefined current intensity), but this may optionally also relate to events outside of the electrosurgical generator 1, for example at the electrosurgical instrument 16. Thus, for example, a corresponding signal for the onset of plasma ignition at the instrument tip may be detected and transmitted to the electrosurgical generator via the data line 13, this then being evaluated by the event detector 53 in order to subsequently to trigger a switchover, for example. —However, the event detector 53 is not absolutely mandatory; for example, a time controller may alternatively or additionally be provided. To this end, a time controller 52 is preferably provided at the processor 5. Consequently, various segments of the operating sequence may follow one another under time control and appropriate switchover(s) of the configuration of the measurement monitors 7, 8 may be undertaken. Consequently, the measurement monitors 7, 8 are under external control in relation to their configuration and presently consequently also in relation to their measurement range, specifically by way of the processor 5.

Further, a control device 54 may be provided in the processor 5. It is designed to read a machine-readable instrument identity indicator, which is saved in the memory 17 of the electrosurgical instrument 16. Consequently, it is possible to verify whether this electrosurgical instrument 16 is enabled for the operation at the electrosurgical generator 1 and/or which of the operating sequences 61, 62, 63 are enabled. Should this not be the case, the operation of the electrosurgical instrument 16 is blocked by the processor 5 or only operating sequences 61, 62, 63 appropriate for the instrument 16 are enabled.

Further, a state detector 55 and an optional replacement switching unit 56 are provided in the processor 5. The state detector 55 is designed to monitor the measurement monitors 7, 8 in their different configurations I, II, III in respect of correct functionality. Thus, it is possible to identify a defect or a fault. The affected configuration or configurations are blocked, for example by placing a corresponding blocking feature, as depicted in the switching state matrix 59 according to FIG. 4 (see in particular the last column therein). Optionally, in the case of such a block, the replacement switching unit 56 may determine, by way of replacement, a different configuration with a larger measurement range, into which there is a subsequent switch rather than into the defective/faulty configuration. Hence, the operation of the electrosurgical generator 1 can be continued, albeit with a slightly reduced measurement accuracy as a result of the excessive measurement range of the configuration switched as a replacement. This creates a failsafe mode for the electrosurgical generator 1.

An alternative embodiment to the switchable measurement monitors is depicted in FIG. 5. In this case, the measurement monitor 7' for voltage comprises a measurement amplifier 75, the operating parameters of which, in particular the measurement range of which, are defined by means of the different signal processing units 71, 72, 73. In respect of its measurement range, the measurement monitor 7' is thus switchable between three configurations I, II, III, as is also depicted in the table in FIG. 4. A corresponding statement applies to the measurement monitor 8' for current with its measurement amplifier 85 and different signal processing units 81, 82, 83. In this embodiment, the switchover according to the invention can be realized with little additional outlay for the measurement monitors.

The invention claimed is:

1. An electrosurgical generator for supplying power to an electrosurgical instrument by way of radiofrequency AC voltage, comprising an inverter for high voltage, which is led via an output line to an output to a connector of the electrosurgical instrument, a measurement system which comprises at least one measurement monitor for a physical parameter at the output or at the electrosurgical instrument, and an operation controller which controls the inverter on a basis of at least one predefined operating sequence,
  wherein
    the measurement monitor for the physical parameter is switchable between a plurality of different configurations which differ in terms of their measurement range,
    the operation controller interacting with the measurement system such that one of the different configurations of the measurement monitor is switched in each case, by control command of the operating sequence.

2. The electrosurgical generator as claimed in claim 1, wherein the measurement monitor is embodied as a measurement monitor for a output voltage and is switchable between a plurality of different configurations which differ in terms of their voltage measurement range, and/or
  the measurement monitor is embodied as a measurement monitor for the output current and is switchable between a plurality of different configurations which differ in terms of their current measurement range.

3. The electrosurgical generator as claimed in claim 1, wherein the at least one predefined operating sequence is selectable by a user from a set of predetermined operating sequences.

4. The electrosurgical generator as claimed in claim 1, wherein the at least one predefined operating sequence and/or the predefined operating sequences each comprise control data for an automated selection and switching of the plurality of different configurations,
  with the plurality of different configurations being switched in a predetermined sequence, according to which the plurality of different configurations of the measurement monitor or monitors are selected in succession, with sequence and/or times of a switchover between the plurality of different configurations being determined by the at least one predefined operating sequence.

5. The electrosurgical generator as claimed in claim 4, wherein the operating sequences comprise time control data which each specify times for connecting up and/or switching between the different configurations of the measurement monitors.

6. The electrosurgical generator as claimed in claim 4, wherein the operating sequences comprise event control data which each specify event conditions for connecting up and/or switching between the different configurations of the measurement monitor or monitors.

7. The electrosurgical generator as claimed in claim 6, wherein signal feedback is provided for at least one event condition for a signal for a temperature present at the electrosurgical instrument for a clamping force at a bipolar electrode of the electrosurgical instrument, for the force exerted by the electrosurgical instrument on tissue to be treated, for identifying carbon at the electrosurgical instrument and/or for identifying an ignition state of plasma at the electrosurgical instrument.

8. The electrosurgical generator as claimed in claim 1, wherein a switchover of configurations of one of the measurement monitors is implemented independently of a switchover of configurations of another of the measurement monitors.

9. The electrosurgical generator as claimed in claim 1, wherein a switching state matrix is provided, in which admissible configurations of the measurement monitor or monitors are defined.

10. The electrosurgical generator as claimed in claim 1, wherein the electrosurgical generator further comprises a processor and a computer-readable data medium on which instructions are stored, the instructions causing the at least one predefined operating sequence to be carried out when executed by the processor.

11. The electrosurgical generator as claimed in claim 10, wherein the at least one predefined operating sequence is configured as a data set with structured data, with the structured data comprising switching control data for connecting up the plurality of different configurations of the measurement monitors.

12. A system comprising an electrosurgical generator as claimed in claim 1 and an electrosurgical instrument, wherein
  the predefined operating sequence is selectable from a set of operating sequences, which are saved in the electrosurgical generator and/or the electrosurgical instrument.

13. The system as claimed in claim 12, wherein the electrosurgical instrument includes a machine-readable instrument identity indicator, and the system comprises a control device which enables one or more operating sequences from the set of operating sequences depending on the machine-readable instrument identity indicator.

14. A method for operating an electrosurgical generator for supplying power to an electrosurgical instrument by way of radiofrequency AC voltage, the electrosurgical generator comprising an inverter for high voltage, which is led via an output line to an output to a connector of the electrosurgical instrument, a measurement system which comprises at least one measurement monitor for a physical parameter at the output or at the electrosurgical instrument, with the inverter being controlled by an operation controller on a basis of at least one predefined operating sequence, the method comprising:

switching during operation between a plurality of different switchable configurations of the measurement monitor which differ in terms of their measurement range, with the switching of a respective one of the different switchable configurations of the measurement monitor for the physical parameter being controlled by control command of the operating sequence.

15. The method as claimed in claim 14, further comprising selecting the operating sequence from a set of operating sequences which are saved in the electrosurgical generator or the electrosurgical instrument.

16. The method as claimed in claim 15, wherein one or more operating sequences from the set of operating sequences are enabled depending on a machine-readable instrument identity indicator which characterizes the electrosurgical instrument.

17. A method for operating the electrosurgical generator according to claim 4 for supplying power to the electrosur-gical instrument by way of radiofrequency AC voltage, the electrosurgical generator comprising the inverter for high voltage, which is led via the output line to the output to a connector of the electrosurgical instrument, a measurement system which comprises the measurement monitor for the physical parameter at the output or at the electrosurgical instrument, with the inverter being controlled by an operation controller on a basis of the predefined operating sequence, the method comprising:

switching during operation between a plurality of different switchable configurations of the measurement monitor which differ in terms of their measurement range, with the switching of a respective one of the different configurations of the measurement monitor for the physical parameter being controlled by control command of the operating sequence.

\* \* \* \* \*